United States Patent
Nakamura

(10) Patent No.: US 12,426,935 B2
(45) Date of Patent: Sep. 30, 2025

(54) MEDICAL TREATMENT TOOL

(71) Applicant: OLYMPUS CORPORATION, Tokyo (JP)

(72) Inventor: Takashi Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1071 days.

(21) Appl. No.: 17/132,131

(22) Filed: Dec. 23, 2020

(65) Prior Publication Data

US 2021/0106373 A1     Apr. 15, 2021

Related U.S. Application Data

(63) Continuation of application No. PCT/JP2018/025379, filed on Jul. 4, 2018.

(51) Int. Cl.
*A61B 18/14*      (2006.01)
*A61B 17/32*      (2006.01)
(Continued)

(52) U.S. Cl.
CPC .... *A61B 18/085* (2013.01); *A61B 17/320092* (2013.01); *A61B 2017/320093* (2017.08);
(Continued)

(58) Field of Classification Search
CPC .............. A61B 18/085; A61B 18/1442; A61B 2018/00404; A61B 2018/00589;
(Continued)

(56) References Cited

U.S. PATENT DOCUMENTS 7,329,257 B2 * 2/2008 Kanehira ............... A61B 46/23
606/45
2003/0171747 A1    9/2003 Kanehira et al.
(Continued)

FOREIGN PATENT DOCUMENTS

EP          3222239 A1    9/2017
JP      S54-060972 U    4/1979
(Continued)

OTHER PUBLICATIONS

International Search Report dated Sep. 18, 2018 issued in PCT/JP2018/025379.
(Continued)

*Primary Examiner* — Thomas A Giuliani
(74) *Attorney, Agent, or Firm* — Scully, Scott, Murphy & Presser, P.C.

(57) ABSTRACT

A medical treatment tool includes: a grasping portion having a first jaw and a second jaw; a plate-shaped blade that is provided in the first jaw and that has a thickness direction; a heater that supplies, to the first blade, thermal energy for treating a tissue grasped by the grasping portion; an energy insulating member that is arranged such that only an output surface of the blade, which comes into contact with the tissue, is exposed and that blocks leakage of the thermal energy to an outside of the first jaw; and first wiring that supplies electrical energy to the heater, wherein the blade, the heater, and the first wiring are arranged so as to be laminated in the thickness direction, and an area of a supply surface where the heater supplies the thermal energy to the blade is larger than an area of the output surface.

16 Claims, 15 Drawing Sheets

(51) Int. Cl.
*A61B 18/08* (2006.01)
*A61B 18/00* (2006.01)

(52) U.S. Cl.
CPC .............. *A61B 2018/00101* (2013.01); *A61B 2018/00595* (2013.01); *A61B 2018/00607* (2013.01); *A61B 2018/0063* (2013.01)

(58) Field of Classification Search
CPC ........... A61B 2018/00595; A61B 2018/00601; A61B 2018/00607; A61B 2018/0063; A61B 2018/00994; A61B 2018/126; A61B 17/320092; A61B 2017/320093
USPC ...... 606/27–31, 41, 50–52; 607/98, 99, 113, 607/115, 116
See application file for complete search history.

(56) References Cited

U.S. PATENT DOCUMENTS

| | | | |
|---|---|---|---|
| 2003/0187429 A1* | 10/2003 | Karasawa | A61B 18/085 606/29 |
| 2004/0078035 A1 | 4/2004 | Kanehira et al. | |
| 2005/0021017 A1 | 1/2005 | Karasawa et al. | |
| 2005/0113826 A1* | 5/2005 | Johnson | A61B 18/1442 606/45 |
| 2006/0271038 A1 | 11/2006 | Johnson et al. | |
| 2008/0039835 A1 | 2/2008 | Johnson et al. | |
| 2008/0045947 A1 | 2/2008 | Johnson et al. | |
| 2008/0195093 A1 | 8/2008 | Couture et al. | |
| 2010/0179543 A1 | 7/2010 | Johnson et al. | |
| 2011/0178519 A1 | 7/2011 | Couture et al. | |
| 2012/0233844 A1 | 9/2012 | Johnson et al. | |
| 2014/0094795 A1* | 4/2014 | Keller | A61B 18/1445 606/34 |
| 2014/0288553 A1 | 9/2014 | Johnson et al. | |
| 2017/0000556 A1* | 1/2017 | Morisaki | A61B 18/1206 |
| 2017/0156788 A1 | 6/2017 | Johnson et al. | |
| 2017/0172643 A1* | 6/2017 | Takashino | A61B 18/085 |
| 2017/0245923 A1 | 8/2017 | Takashino et al. | |
| 2020/0129227 A1 | 4/2020 | Johnson et al. | |
| 2020/0337761 A1 | 10/2020 | Johnson et al. | |

FOREIGN PATENT DOCUMENTS

| | | |
|---|---|---|
| JP | 2001-198137 A | 7/2001 |
| JP | 2004-188012 A | 7/2004 |
| JP | 2004-329764 A | 11/2004 |
| JP | 2005-40215 A | 2/2005 |
| JP | 2008-212663 A | 9/2008 |
| JP | 2017-225882 A | 12/2017 |
| WO | 2016/080147 A1 | 5/2016 |

OTHER PUBLICATIONS

English translation of JP S60-4487 Y2 (corresponding to JP S54-060972 U).

* cited by examiner

MEDICAL TREATMENT TOOL

CROSS-REFERENCE TO RELATED APPLICATIONS

This is a continuation of International Application PCT/JP2018/025379, with an international filing date of Jul. 4, 2018, which is hereby incorporated by reference herein in its entirety.

TECHNICAL FIELD

The present invention relates to a medical treatment tool.

BACKGROUND ART

There is a known treatment tool in which tissue is sandwiched between a blade provided with a heater and a receiving member disposed at a position opposing the blade, and the tissue is sealed and incised as a result of heat being applied to the tissue from the blade heated by the heater (for example, see Patent Literature 1).

CITATION LIST

Patent Literature

{PTL 1} Japanese Unexamined Patent Application, Publication No. 2001-198137

SUMMARY OF INVENTION

One aspect of the present invention is directed to a medical treatment tool comprising: a grasping portion having a first jaw and a second jaw that can be opened and closed; a plate-shaped first blade that is provided in the first jaw and that has a thickness direction; at least one heater that supplies, to the first blade, thermal energy for treating a tissue grasped by the grasping portion; an energy insulating member that is arranged such that only an output surface of the first blade, which comes into contact with the tissue, is exposed and that blocks leakage of the thermal energy to an outside of the first jaw; and first wiring that supplies electrical energy to the heater, wherein the first blade, the heater, and the first wiring are arranged so as to be laminated in the thickness direction, and an area of at least one supply surface where the heater supplies the thermal energy to the first blade is larger than an area of the output surface.

Another aspect of the present invention is directed to a medical treatment tool comprising: a grasping portion having a first jaw and a second jaw that can be opened and closed; a plate-shaped blade that is provided in the first jaw and that has a thickness direction; an energy supply portion that supplies, to the blade, treatment energy for treating a tissue grasped by the grasping portion; an energy insulating member that is arranged such that only an output surface of the blade, which comes into contact with the tissue, is exposed and that blocks leakage of the treatment energy to an outside of the first jaw; and first wiring that supplies electrical energy to the energy supply portion, wherein the blade, the energy supply portion, and the first wiring are arranged so as to be laminated in the thickness direction, and an area of a supply surface where the energy supply portion supplies the treatment energy to the blade is larger than an area of the output surface.

DESCRIPTION OF EMBODIMENT

A medical treatment tool 1 according to an embodiment of the present invention will be described below with reference to the drawings.

Figure 1:
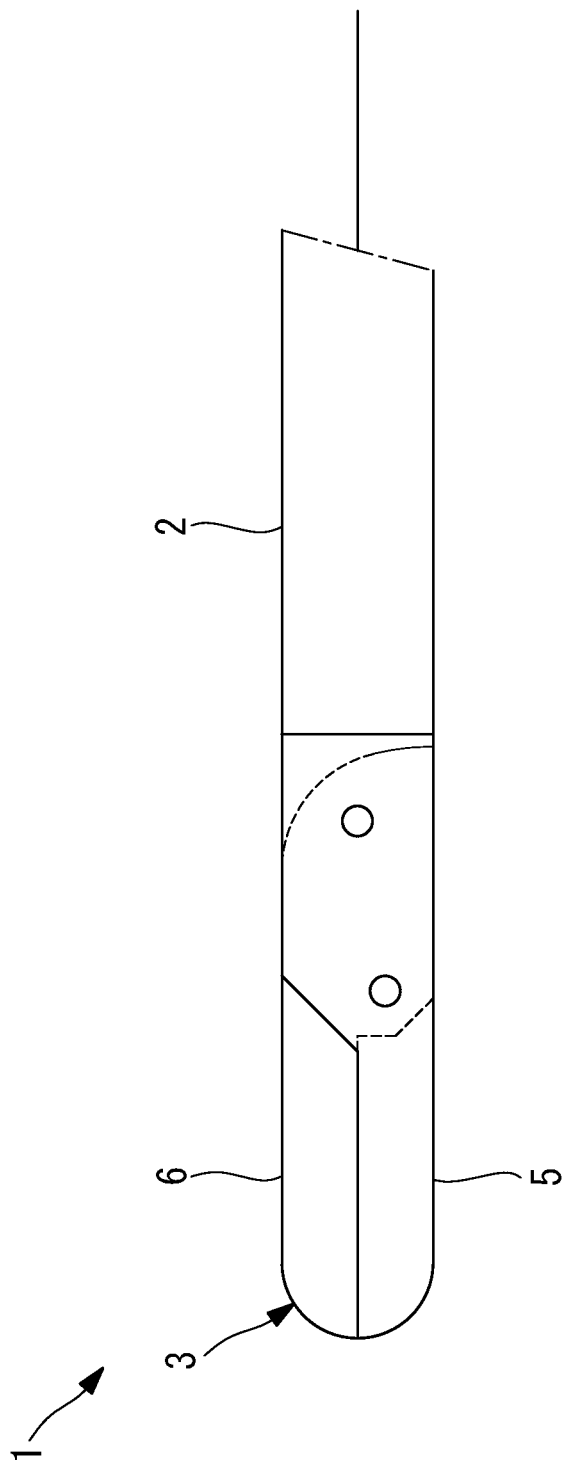
FIG. 1 is a front view partially showing a distal end portion of a medical treatment tool according to an embodiment of the present invention.

As shown in FIG. 1, the medical treatment tool 1 according to this embodiment is thermocoagulation incision forceps provided with: a grasping portion 3 at the distal end of an insertion portion 2 having a longitudinal axis; and an operating portion at the base end of the insertion portion 2.

The grasping portion 3 includes a first jaw 5 and a second jaw 6 that are coupled so as to be pivotable about an axis orthogonal to the longitudinal axis.

Figure 2:
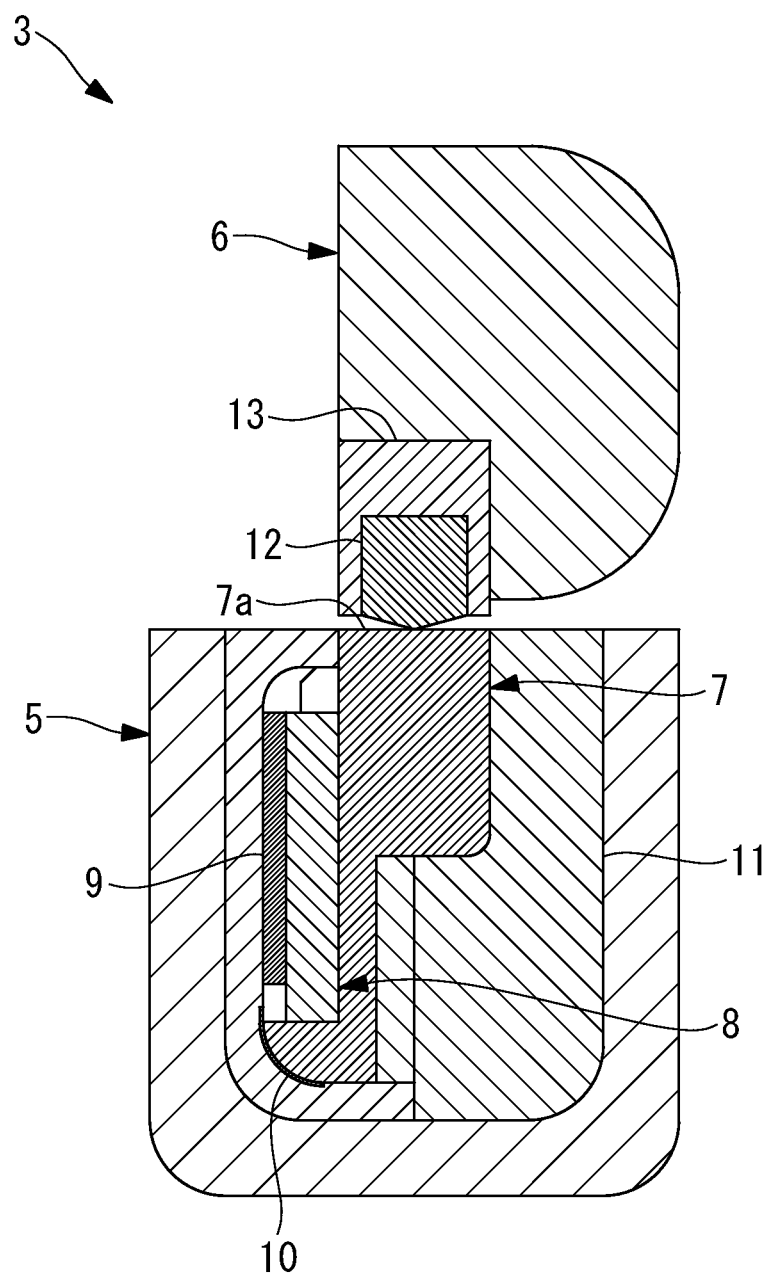
FIG. 2 is a cross-sectional view of a grasping portion showing the medical treatment tool in FIG. 1.

As shown in FIG. 2, the first jaw 5 includes: a blade 7 composed of a plate-shaped metal; a plate-shaped heater (energy supply portion, energy conversion portion) 8 that is in close contact with a surface of the blade 7; first wiring (energy supply portion, electrical-energy supply portion) 9 that supplies electrical energy to the heater 8; second wiring (electrical-energy supply portion) 10 that supplies a current to the blade 7; and a thermoelectrical insulating member (energy insulating member) 11 that exposes only one surface (output surface) 7a along the plate thickness direction of the blade 7 and covers other surfaces of the blade 7. The thermoelectrical insulating member 11 is composed of, for example, a resin material such as PEEK or LCP.

Figure 3:
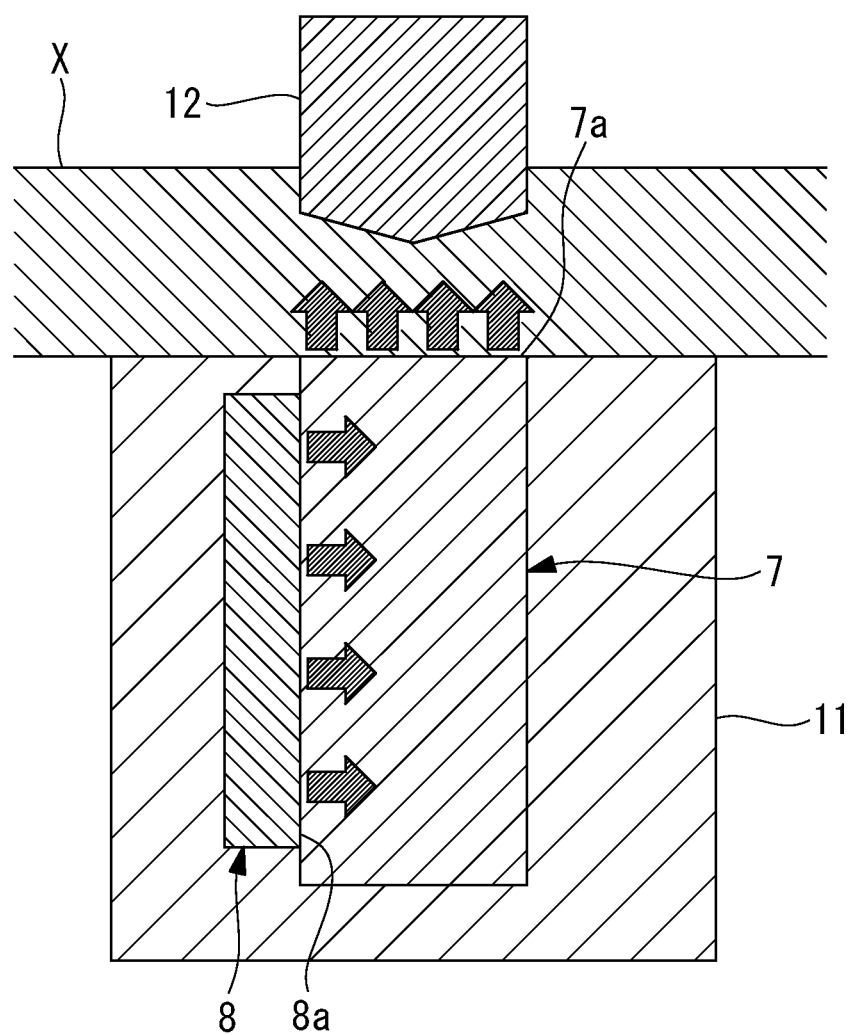
FIG. 3 is a cross-sectional view schematically showing the grasping portion in FIG. 2.

As shown in FIG. 3, the plate-shaped heater 8 is provided such that one surface (supply surface) 8a along the width direction is in close contact with one surface along the width direction of the blade 7. The area of the supply surface 8a is set to be sufficiently larger than the area of the output surface 7a of the blade 7.

The first wiring 9 is composed of a flexible wiring board (conductive member). The first wiring 9 is disposed at such a position that the first wiring 9 is in close contact with a flat surface along the width direction of the heater 8. By doing so, the blade 7, the heater 8, and the first wiring 9 are arranged in a laminated state in the thickness direction, whereby the overall thickness dimension is suppressed.

Figure 4:
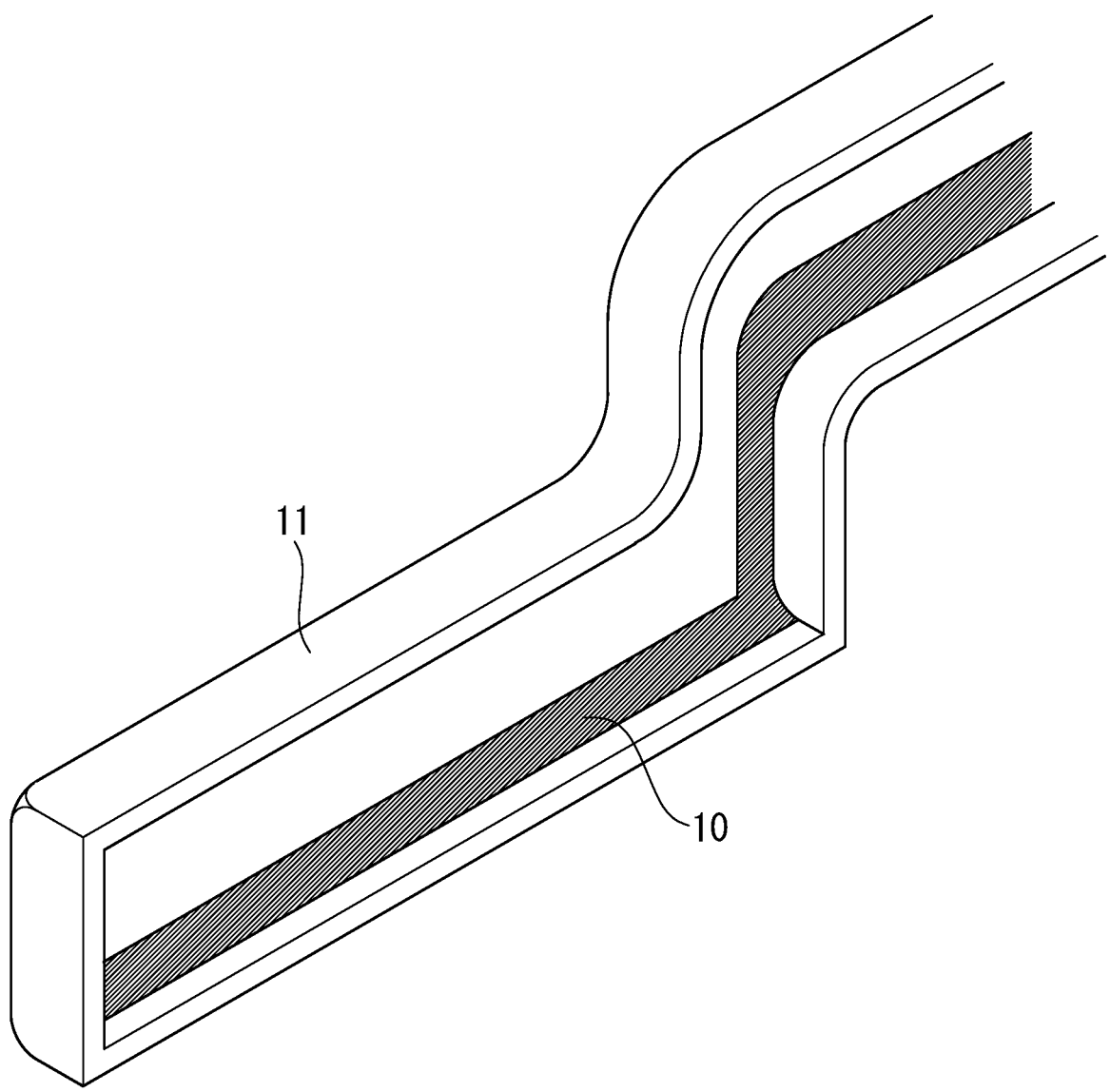
FIG. 4 is a perspective view showing an example of second wiring provided in the grasping portion in FIG. 2.

As shown in FIG. 4, the second wiring 10 is formed on an inner surface (surface) of the thermoelectrical insulating member 11 by means of, for example, the MID (Molded Interconnect Device) technology, and is composed of a conductive thin film that conducts the electrical energy.

As shown in FIG. 2, the second jaw 6 includes a blade 12 disposed at such a position that tissue X is sandwiched between the output surface 7a of the blade 7 in the first jaw 5 and the blade 12. A surface opposing the output surface 7a of the blade 7 in the first jaw 5 has a convex shape that protrudes most at the center in the width direction. The surfaces of the blade 12 in the second jaw 6, excluding the opposing surface, are also covered with a thermoelectrical insulating member 13.

The thermoelectrical insulating member 13 of the second jaw 6 has a shape in which the blade 12 is exposed in at least one direction intersecting the pivoting direction.

The operation of the thus-configured medical treatment tool 1 according to this embodiment will be described below.

With the medical treatment tool 1 according to this embodiment, the first jaw 5 and the second jaw 6 are pivoted relative to each other; in a state in which the output surface 7a of the blade 7 and the opposing surface of the blade 12 are separated from each other, tissue X is disposed between the output surface 7a and the opposing surface; and the output surface 7a and the opposing surface are brought close to each other, whereby the tissue X is sandwiched between the output surface 7a and the opposing surface.

In this state, when a current is supplied to the blade 7 via the second wiring 10, the blade 7 in the first jaw 5 functions as a monopolar electrode, supplying the current to the tissue X from the output surface 7a, and the tissue X in the vicinity of the blade 7 is cauterized and sealed.

Subsequently, electrical energy is supplied to the heater 8 via the first wiring 9, and the electrical energy is converted into thermal energy (treatment energy) by the heater 8. The converted thermal energy passes through the supply surface 8a of the heater 8 and is supplied to the blade 7, which is in close contact with the supply surface 8a, thereby heating the blade 7.

Because only the output surface 7a of the blade 7 is exposed and the surfaces other than the output surface 7a are covered with the thermoelectrical insulating member 11, the thermal energy supplied to the blade 7 is supplied to the tissue X via the output surface 7a. In this case, the output surface 7a of the blade 7 in the first jaw 5, which sandwiches the tissue X with the opposing surface of the blade 12 in the second jaw 6, has an area sufficiently smaller than that of the supply surface 8a where the thermal energy is supplied to the blade 7 from the heater 8; thus, the heat supplied to the blade 7 from the wide supply surface 8a of the heater 8 is output to the tissue X from the output surface 7a, which is narrower than the supply surface 8a, with an increased heat flux density.

In other words, leakage of the thermal energy from the blade 7 is suppressed by the thermoelectrical insulating member 11, and the thermal energy is supplied to the tissue X with an increased heat flux density; therefore, it is possible to effectively cut the tissue X. In addition, there is an advantage in that it is possible to reduce the size of the heater 8 that supplies the thermal energy for cutting the tissue X.

As described above, with the medical treatment tool 1 according to this embodiment, the plate-shaped heater 8 is laminated on the plate-shaped blade 7 in the plate thickness direction, and in addition, the first wiring 9 that supplies the electrical energy to the heater 8 is composed of a flexible wiring board and is laminated on the heater 8 in the plate thickness direction; therefore, it is possible to achieve a thickness reduction of the first jaw 5. Furthermore, the current is also supplied to the blade 7 by means of the second wiring 10, which is a conductive thin film formed by employing the MID technology; thus, the thermocoagulation incision forceps can be configured without sacrificing the thinness of the first jaw 5.

Furthermore, with the arrangement in which the area of the output surface 7a of the blade 7 is set to be smaller than the area of the supply surface 8a of the heater 8, there is an advantage in that it is possible to achieve a size reduction of the heater 8, in particular, the thickness reduction of the heater 8, and that the first jaw 5 can be configured to be even thinner.

In addition, the thermoelectrical insulating member 13 of the second jaw 6 has a shape in which the blade 12 is exposed in at least one direction intersecting the pivoting direction; thus, in a state in which the tissue X is sandwiched between the blade 7 in the first jaw 5 and the blade 12 in the second jaw 6, it is possible to visually recognize the blade 12 in the second jaw 6 from the outside. By doing so, there is an advantage in that it is possible to perform incision while confirming, in a more accurate manner, the position at which the tissue X is sandwiched.

Figure 5:
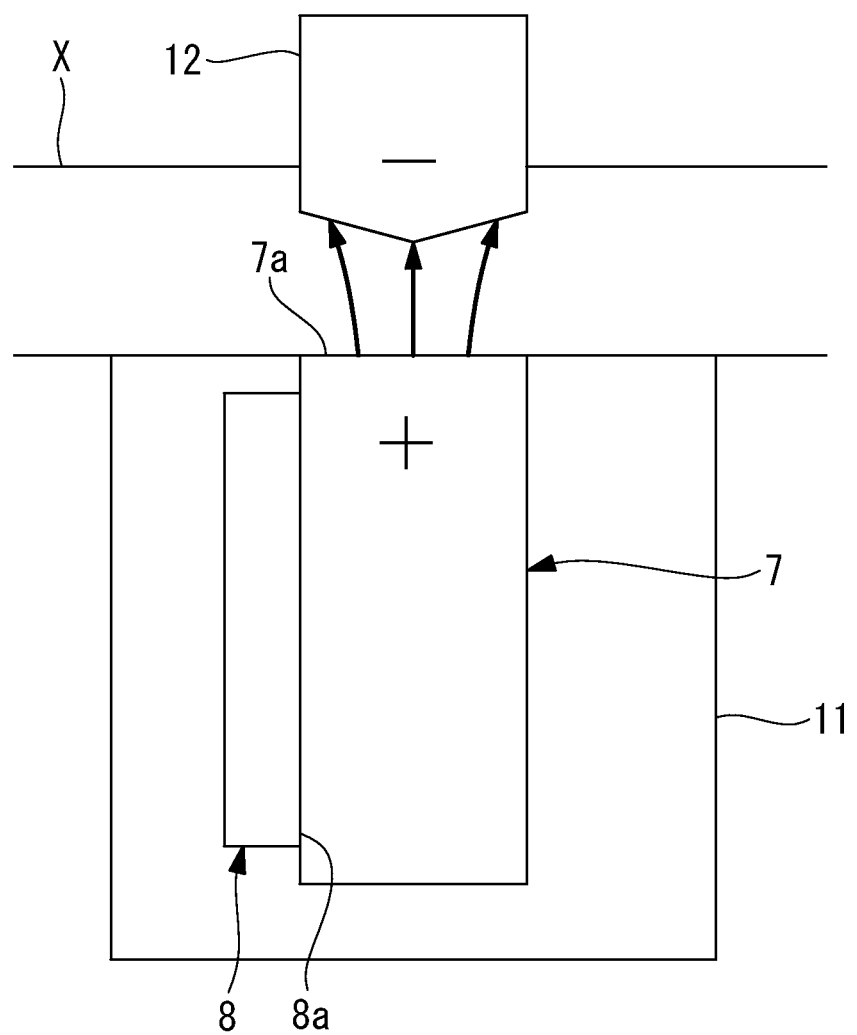
FIG. 5 is a schematic cross-sectional view of a grasping portion showing a first modification of the medical treatment tool in FIG. 1.

Note that, although the monopolar electrode structure in which only the blade 7 in the first jaw 5 is used as an electrode is employed in this embodiment, alternatively, as shown in FIG. 5, it is permissible to employ a bipolar electrode structure in which the blade 7 in the first jaw 5 is used as a first electrode, the blade 12 in the second jaw 6 is used as a second electrode, and a current is made to flow between the blades.

Figure 6:
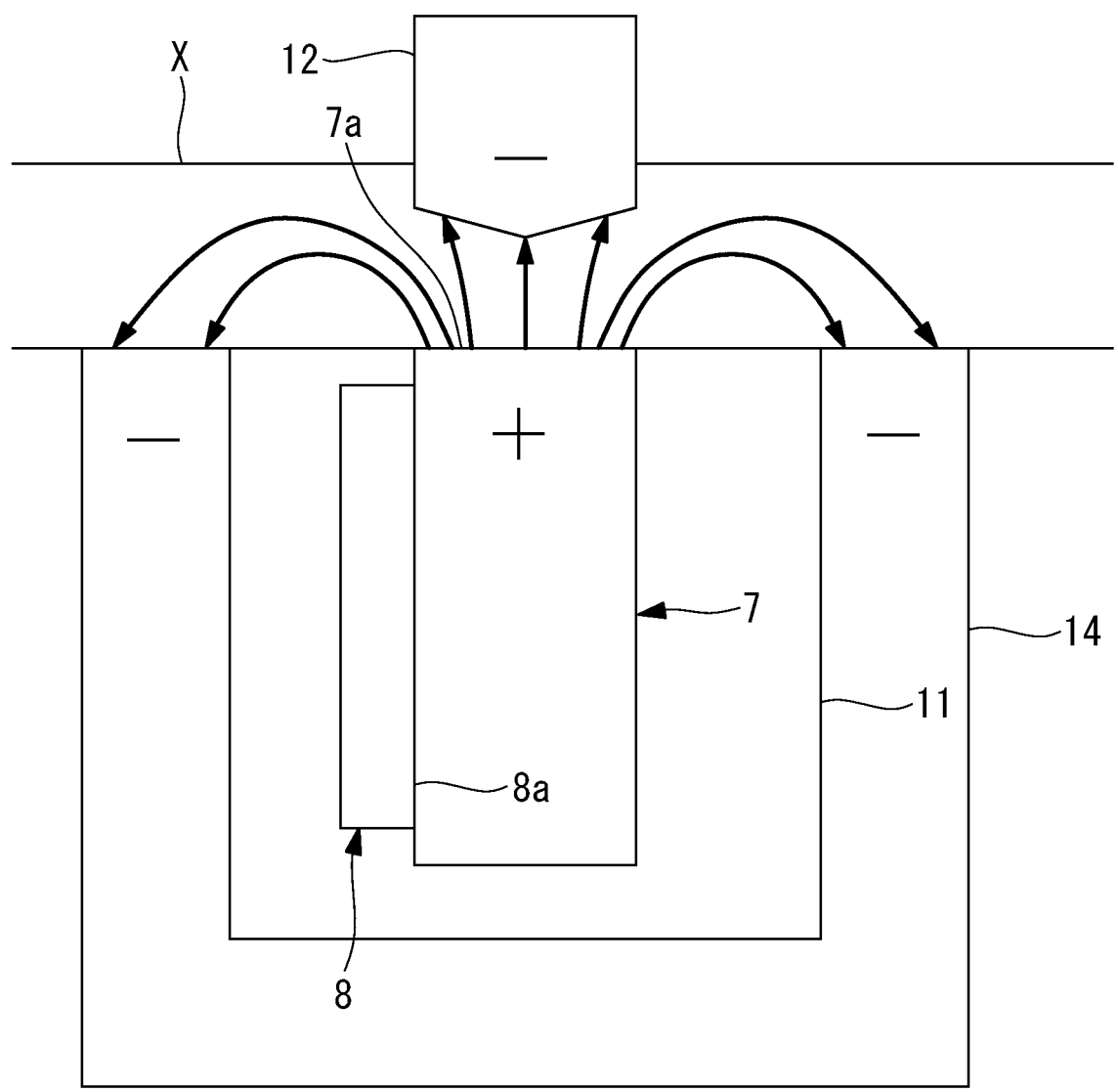
FIG. 6 is a schematic cross-sectional view of a grasping portion showing a second modification of the medical treatment tool in FIG. 1.

In addition, in this case, as shown in FIG. 6, third electrodes 14 may be arranged on both sides sandwiching, in the width direction, the blade 7 serving as the first electrode in the first jaw 5, with the thermoelectrical insulating member 11 interposed therebetween, and a current may also be made to flow between the blade 7 serving as the first electrode and the third electrodes 14. By doing so, there is an advantage in that it is possible to reliably perform sealing by expanding the cauterization range.

In addition, in this embodiment, the blade 12 in the second jaw 6 may be composed of an elastic material having a Young's modulus smaller than that of the blade 7 in the first jaw 5. By doing so, when the tissue X is grasped between the blades 7, 12, it is possible to prevent the problem of the tissue X being unintentionally cut due to the grasping force.

Figure 7:
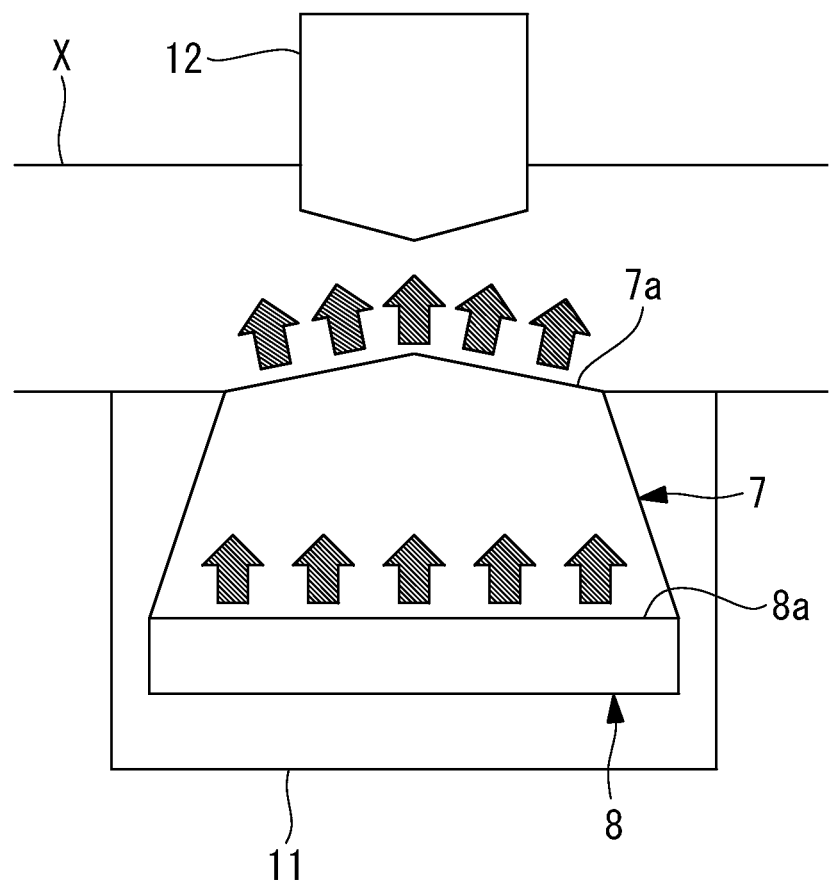
FIG. 7 is a schematic cross-sectional view of a grasping portion showing a third modification of the medical treatment tool in FIG. 1.
Figure 8:
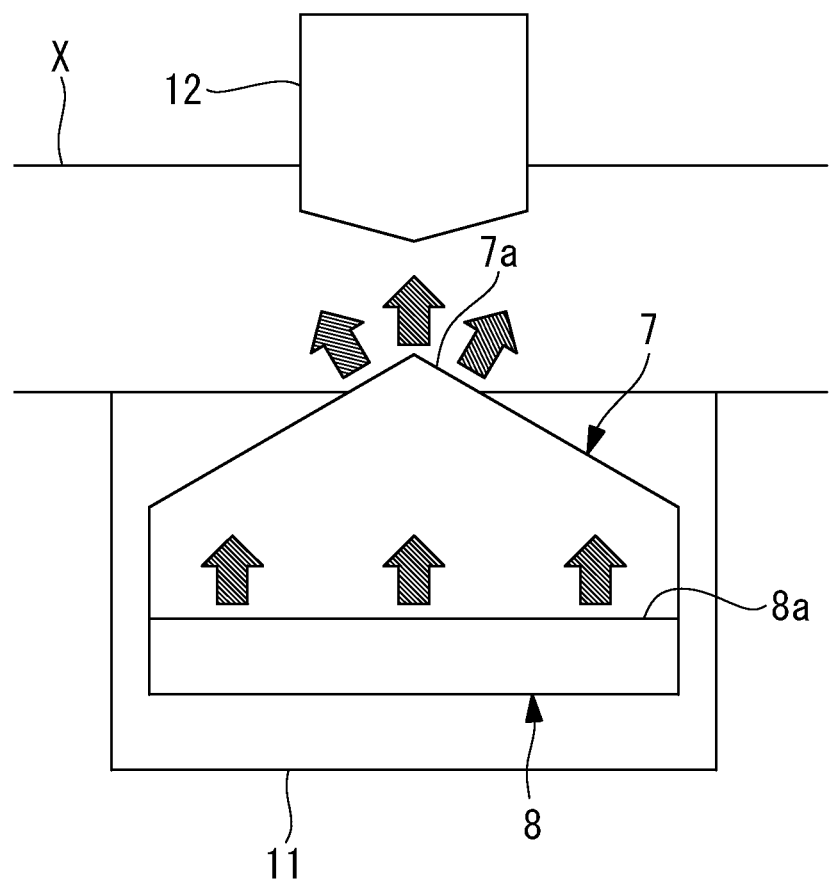
FIG. 8 is a schematic cross-sectional view of a grasping portion showing a fourth modification of the medical treatment tool in FIG. 1.
Figure 9:
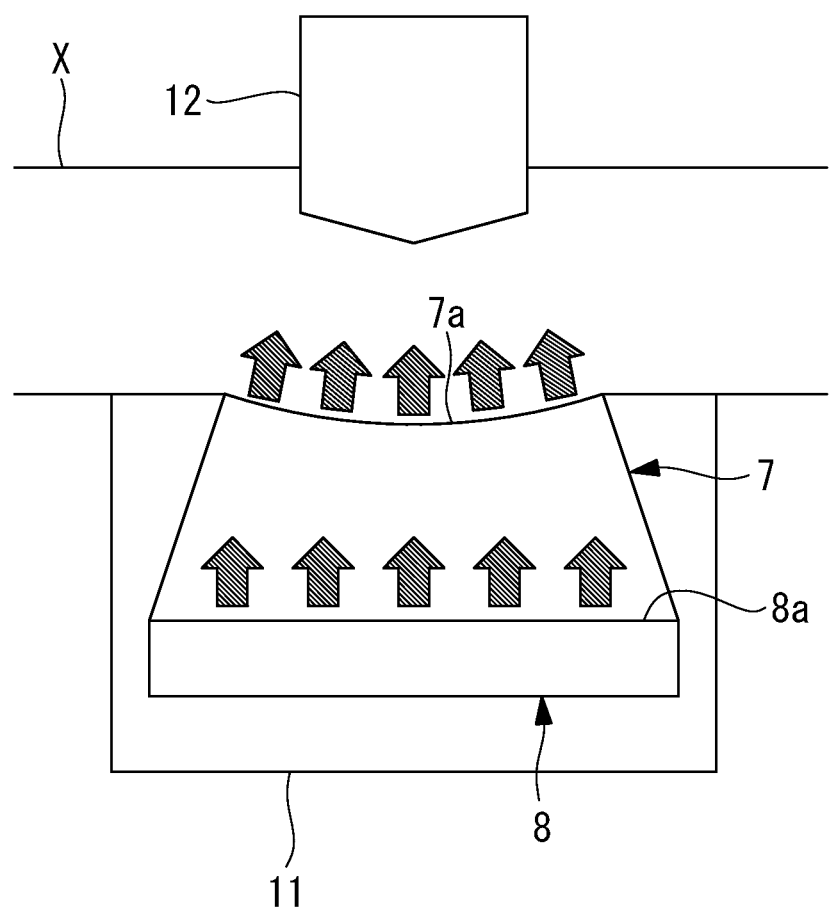
FIG. 9 is a schematic cross-sectional view of a grasping portion showing a fifth modification of the medical treatment tool in FIG. 1.

In addition, although the output surface 7a of the blade 7 in the first jaw 5 is configured to have a planar shape in this embodiment, alternatively, a surface shape of any form may be employed. For example, the output surface 7*a* may be formed in a convex shape as shown in FIGS. 7 and 8, or may be configured to be a concave surface as shown in FIG. 9. By configuring the output surface 7*a* to be a concave surface, there is an advantage in that diffusion of the heat flux can be further suppressed.

In addition, the blade 7 in the first jaw 5 and the heater 8 are configured to have a flat plate shape and are arranged in a laminated state such that the width direction of the first jaw 5 and the plate thickness direction of the blade 7 and the heater 8 are aligned in this embodiment; however, alternatively, the arrangement of the blade 7 and the heater 8 may be changed arbitrarily, as shown in FIGS. 7 and 8, so long as the area of the output surface 7*a* is smaller than the area of the supply surface 8*a* where the thermal energy is supplied from the heater 8.

Figure 10:
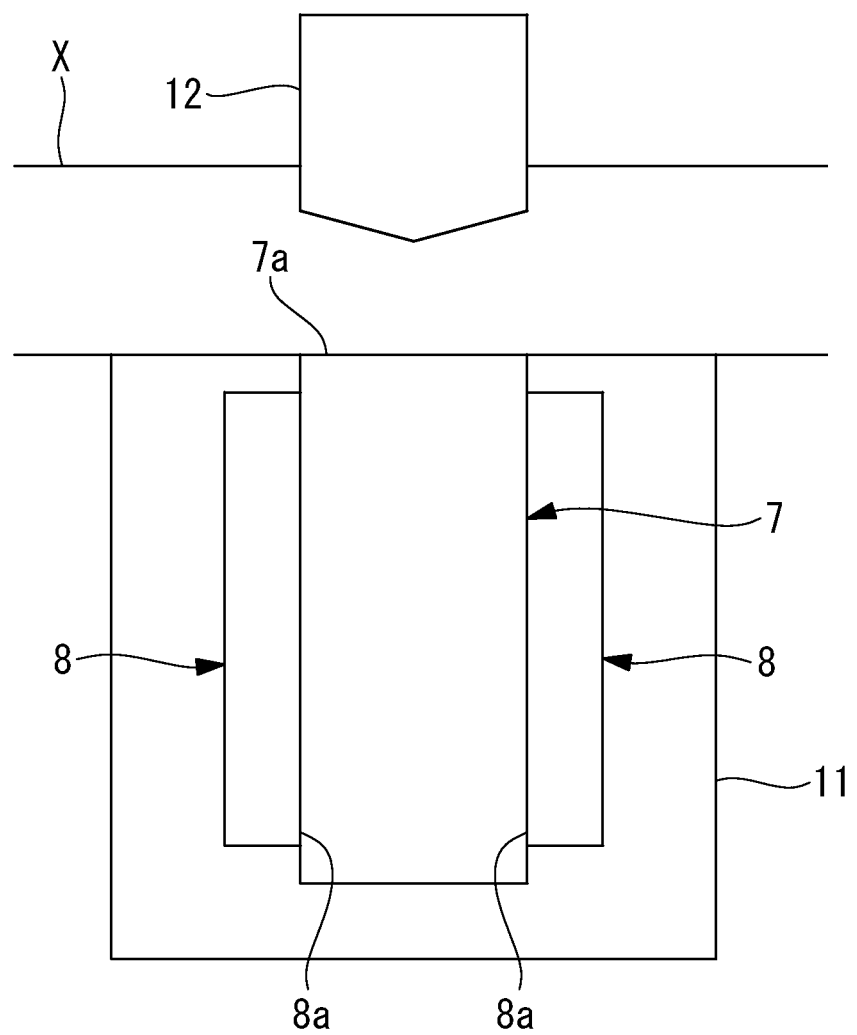
FIG. 10 is a schematic cross-sectional view of a grasping portion showing a sixth modification of the medical treatment tool in FIG. 1.
Figure 11:
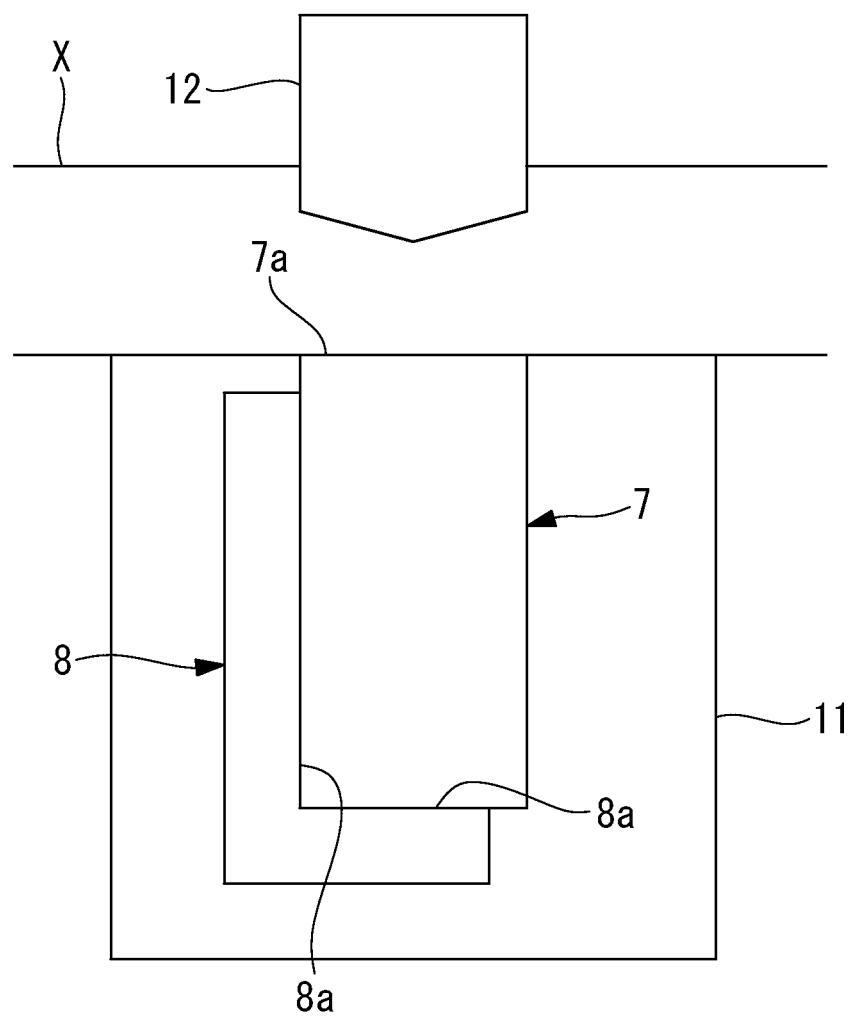
FIG. 11 is a schematic cross-sectional view of a grasping portion showing a seventh modification of the medical treatment tool in FIG. 1.
Figure 12:
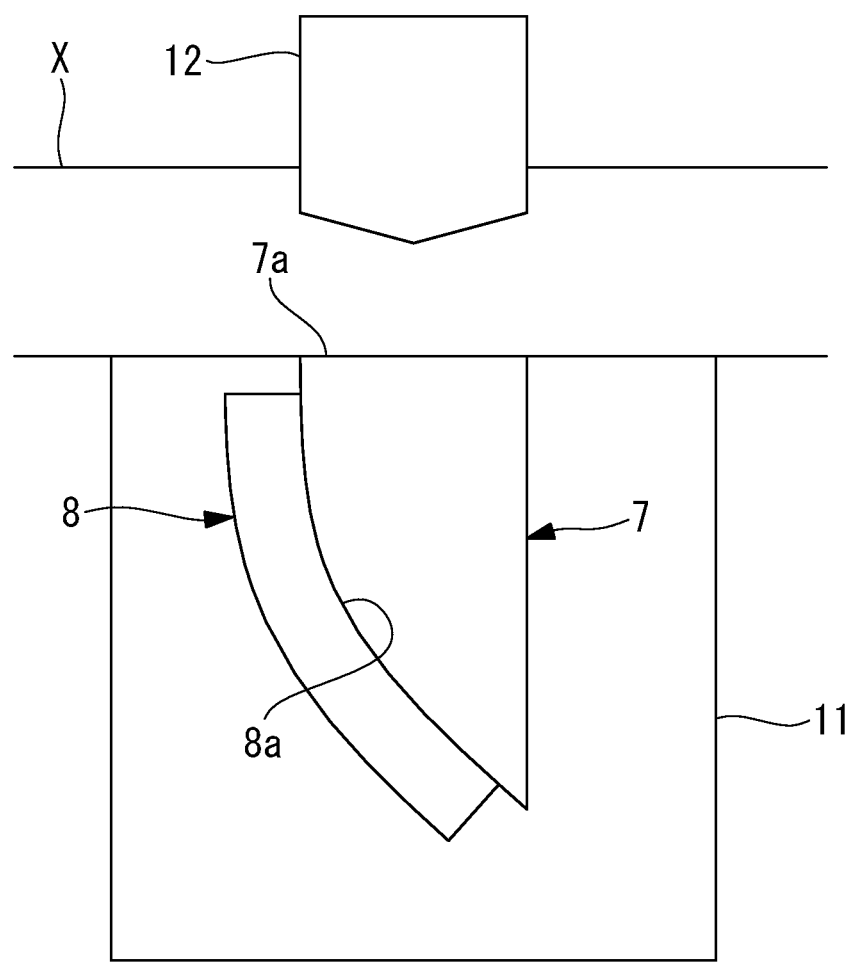
FIG. 12 is a schematic cross-sectional view of a grasping portion showing an eighth modification of the medical treatment tool in FIG. 1.
Figure 13:
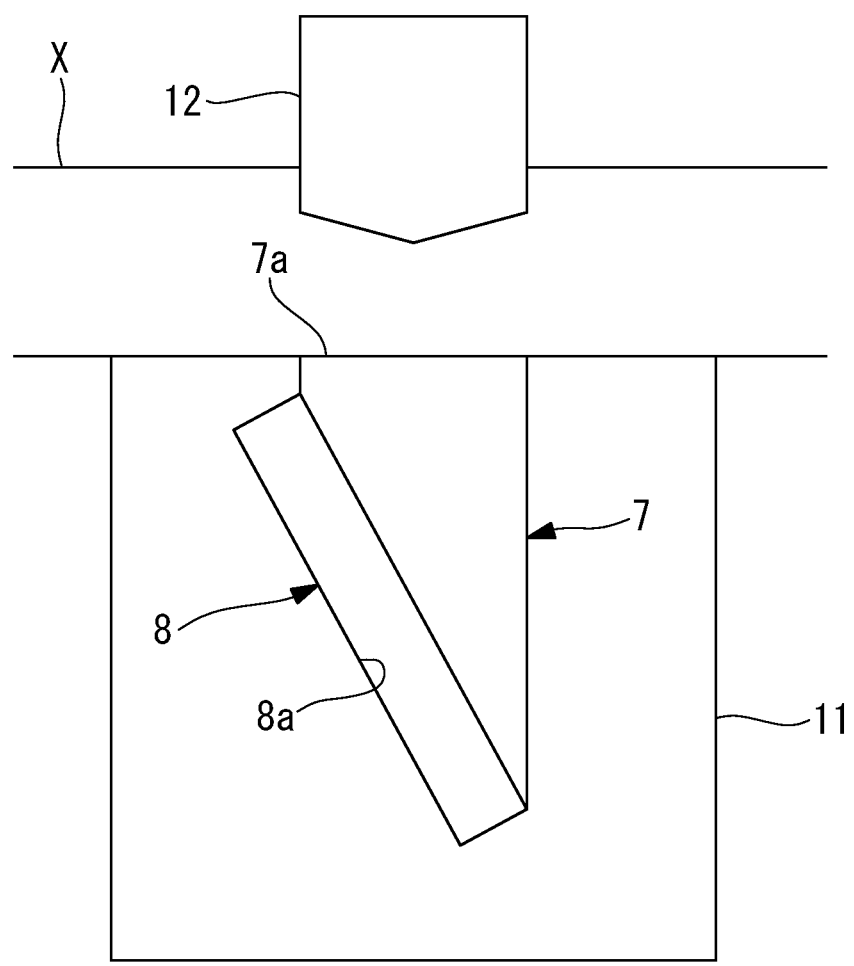
FIG. 13 is a schematic cross-sectional view of a grasping portion showing a ninth modification of the medical treatment tool in FIG. 1.
Figure 14:
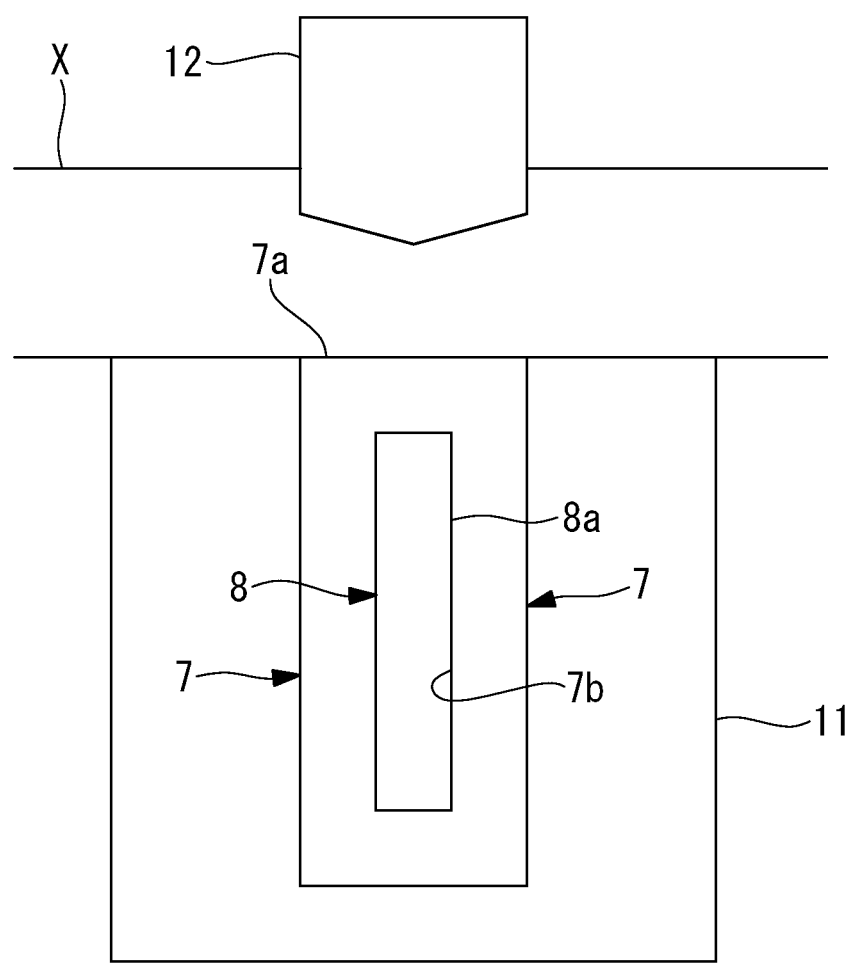
FIG. 14 is a schematic cross-sectional view of a grasping portion showing a tenth modification of the medical treatment tool in FIG. 1.

In addition, although one surface of the heater 8 is set to be the supply surface 8*a* in the example shown in FIG. 2, alternatively, as shown in FIGS. 10 and 11, a plurality of supply surfaces 8*a* may be provided, or the heater 8 may be brought into contact with a plurality of surfaces of the blade 7. In addition, as shown in FIGS. 12 and 13, the surface of the blade 7 with which the supply surface 8*a* is brought into close contact may be configured to be a curved surface or an inclined surface to ensure a larger area for the supply surface 8*a*. In addition, as shown in FIG. 14, the entire peripheral surface of the heater 8 may be set to be the supply surface 8*a* by fitting the heater 8 into a hole 7*b* formed in the blade 7.

Figure 15:
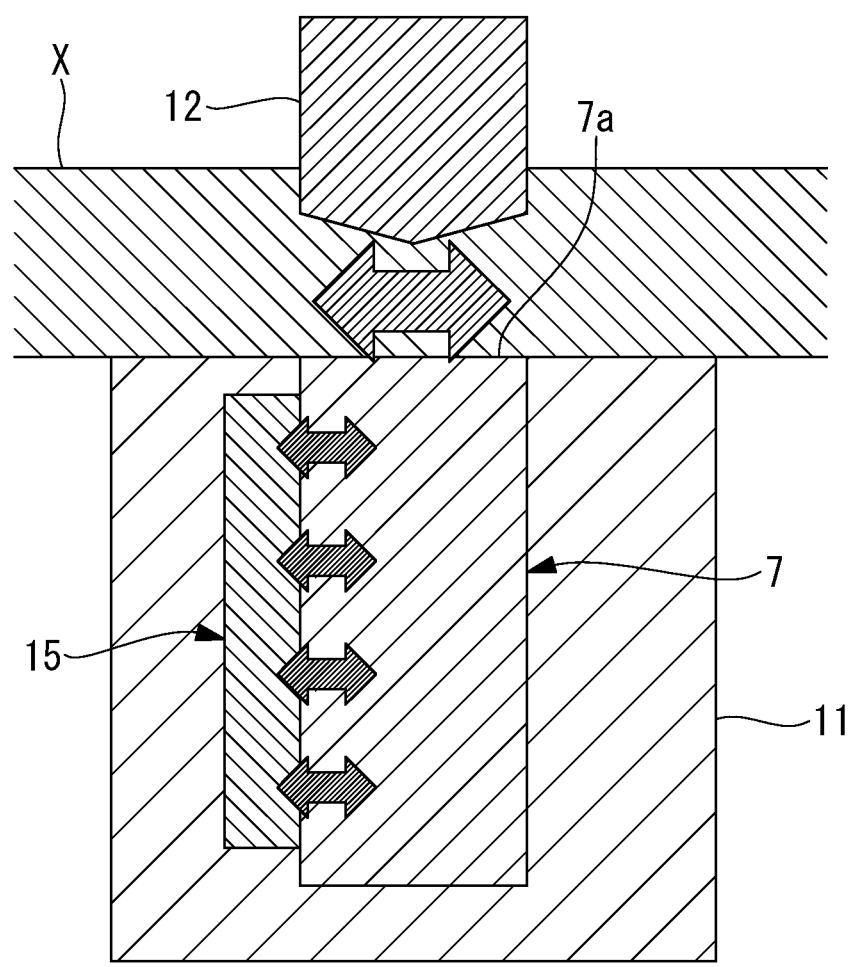
FIG. 15 is a schematic cross-sectional view of a grasping portion showing an eleventh modification of the medical treatment tool in FIG. 1.

In addition, although the heater 8 that converts the electrical energy into the thermal energy is employed as the energy conversion portion in this embodiment, alternatively, as shown in FIG. 15, an ultrasonic vibrator 15 may be employed as the energy conversion portion, and ultrasonic waves may be supplied to the tissue X as the treatment energy.

As a result, the above-described embodiment leads to the following aspect.

An aspect of the present invention is directed to a medical treatment tool including: a grasping portion having a first jaw and a second jaw that can be opened and closed; blades that are respectively provided in the first jaw and the second jaw; and energy supply portions that supply, to the blade in the first jaw, treatment energy for treating tissue sandwiched between the blades, wherein the first jaw includes an energy insulating member that covers the blade in the first jaw to block leakage of the treatment energy to the outside of the first jaw, the energy insulating member is disposed at such a position that only an output surface, which comes into contact with the tissue sandwiched between the blades in the first jaw and the second jaw, is exposed, and the area of a supply surface where the energy supply portion supplies the treatment energy to the first jaw is larger than the area of the output surface.

With this aspect, tissue is disposed between the first jaw and the second jaw of the grasping portion, and by closing the first jaw and the second jaw, the tissue is grasped in a state in which the tissue is sandwiched between the first jaw and the second jaw. In this state, when the energy supply portion supplies the treatment energy to the blade in the first jaw, the treatment energy is supplied to the tissue via the blade, whereby treatment of the tissue can be performed.

The blade in the first jaw is covered with the energy insulating member and only the output surface that comes into contact with the tissue is exposed; thus, the treatment energy is supplied to the tissue via the output surface. In addition, the area of the supply surface where the energy supply portion supplies the treatment energy to the blade is set to be larger than the area of the output surface; therefore, the treatment energy supplied to the blade from the supply surface having a large area is supplied to the tissue in a state in which the energy density is increased when passing through the output surface having a small area. By doing so, it is possible to effectively incise the tissue while reducing the width of the blade in the first jaw sandwiching the tissue together with the blade in the second jaw.

In the abovementioned aspect, the energy supply portion may include: an electrical-energy supply portion that supplies electrical energy; and an energy conversion portion that converts the supplied electrical energy into the treatment energy.

With this configuration, the electrical energy supplied from the electrical-energy supply portion is converted into the treatment energy by the energy conversion portion, and the treatment energy is supplied to the blade in the first jaw.

In the abovementioned aspect, the energy conversion portion may be formed in a flat plate shape having the supply surface on one surface thereof.

With this configuration, the wide supply surface of the plate-shaped energy conversion portion is brought into contact with the blade, and thus, it is possible to supply a greater amount of the treatment energy to the blade while the cross-sectional shape of the first jaw is kept small.

In the abovementioned aspect, the blade in one of the first jaw and the second jaw may include a first electrode that supplies a current to the tissue sandwiched between said blade and the other blade.

With this configuration, the tissue can be sealed by supplying a current to the tissue from the first electrode in a state in which the tissue is sandwiched between the blades in the first jaw and the second jaw.

In the abovementioned aspect, the other blade may include a second electrode that makes a current flow between the first electrode and the second electrode.

With this configuration, by supplying a current to the tissue from the first electrode in a state in which the tissue is sandwiched between the blades in the first jaw and the second jaw, the current supplied to the tissue flows to the second electrode provided in the other blade. By doing so, the tissue can be sealed in a more reliable manner by means of the bipolar system.

In the abovementioned aspect, the first jaw may include: the first electrode; and third electrodes that are arranged on both sides sandwiching the first electrode in a width direction, with an electrical insulating material interposed therebetween, and that make a current flow between the first electrode and the third electrodes.

With this configuration, when a current is supplied to the tissue from the first electrode provided in the blade in the first jaw in a state in which the tissue is sandwiched between the blades in the first jaw and the second jaw, the current flows in an area between the second electrode provided in the second jaw and the third electrodes in the first jaw. Thus, the tissue can be sealed over a wider range.

In the abovementioned aspect, the energy insulating member may be composed of an electrical insulating material, and the electrical-energy supply portion may be formed on a surface of the energy insulating member and may include a conductive thin film that conducts the electrical energy.

With this configuration, it is possible to electrically insulate the blade in the first jaw from the outside by means of the energy insulating member, and to supply the electrical energy to the blade by means of the conductive thin film provided on the surface of the energy insulating member. By doing so, the first jaw can be made thinner.

In the abovementioned aspect, the electrical-energy supply portion may be provided so as to be laminated in a thickness direction of the energy conversion portion, and may include a thin plate-like conductive member that conducts the electrical energy.

With this configuration, the first jaw can be made thinner.

In the abovementioned aspect, the energy conversion portion may have a plurality of the supply surfaces.

With this configuration, it is possible to ensure wide supply surfaces, thereby supplying a greater amount of the treatment energy to the blade, while suppressing the maximum size of the energy conversion portion.

In the abovementioned aspect, the second jaw may have a shape in which the blade is exposed in at least one direction intersecting the opening/closing direction.

With this configuration, it is possible to enhance the visibility of the position of the blade relative to the tissue when the first jaw and the second jaw are closed.

In the abovementioned aspect, the output surface may be a flat surface or a concave surface.

With this configuration, it is possible to suppress diffusion of the treatment energy output from the output surface, thereby efficiently supplying the treatment energy to the tissue.

In the abovementioned aspect, the blade in the second jaw may be made of a material having a Young's modulus smaller than that of the blade in the first jaw.

With this configuration, when the tissue is sandwiched between the first jaw and the second jaw, it is possible to prevent an excessive grasping force from being applied to the tissue by elastically deforming the blade, thereby preventing the tissue from being cut before sealing.

The present invention affords an advantage in that it is possible to effectively incise tissue while reducing the width of a blade sandwiching the tissue.

REFERENCE SIGNS LIST 1 medical treatment tool
3 grasping portion
5 first jaw
6 second jaw
7, 12 blade (first electrode, second electrode)
7a output surface
8 heater (energy supply portion, energy conversion portion)
8a supply surface
9 first wiring (energy supply portion, electrical-energy supply portion, conductive member)
10 second wiring (electrical-energy supply portion, conductive thin film)
11, 13 thermoelectrical insulating member (energy insulating member, electrical insulating material)
14 third electrode
15 ultrasonic vibrator (energy supply portion, energy conversion portion)
X tissue

The invention claimed is:

1. A medical treatment tool comprising: a grasping portion having a first jaw and a second jaw configured to be opened and closed, wherein the first jaw comprises: a first blade; and an electric heater having a supply surface, the electric heater configured to supply thermal energy to the first blade; the first blade having: an output surface facing the second jaw; and a heat receiving surface that contacts the supply surface; the supply surface having an area larger than an area of the output surface; and the supply surface being elongated in an opening and closing direction of the grasping portion.

2. The medical treatment tool according to claim 1, wherein the first blade includes a first electrode configured to supply a current to a tissue sandwiched between the first blade and a second blade, and wherein the second jaw comprises the second blade facing the output surface.

3. The medical treatment tool according to claim 2, wherein the second blade comprises a second electrode, the second blade makes a current flow between the first electrode and the second electrode.

4. The medical treatment tool according to claim 3, wherein the first jaw comprises:
the first electrode; and
third electrodes arranged on both sides sandwiching the first electrode in a width direction intersecting the opening and closing direction of the grasping portion,
wherein an insulator is located between the first electrode and each of the third electrodes, and
the third electrodes make a current flow between the first electrode and the third electrodes.

5. The medical treatment tool according to claim 1, wherein the output surface is a flat surface or a concave surface.

6. The medical treatment tool according to claim 1, wherein the second jaw comprises a second blade facing the output surface, and the second blade is made of a material having a Young's modulus smaller than that of the first blade.

7. The medical treatment tool according to claim 1, wherein the output surface extends along a width direction of the first blade, and the width direction is orthogonal to the opening and closing direction.

8. The medical treatment tool according to claim 1, wherein
the electric heater comprises two electric heaters,
the two electric heaters and the first blade are stacked in a width direction of the first jaw, the width direction being orthogonal to the opening and closing direction, and
the two electric heaters sandwich the first blade in the width direction.

9. The medical treatment tool according to claim 1, further comprising an energy insulator arranged such that only the output surface of the first blade is exposed and that blocks leakage of the thermal energy to an outside of the first jaw; and
wherein the output surface of the first blade is configured to contact a tissue.

10. The medical treatment tool according to claim 9, wherein the energy insulator is composed of an electrical insulating material, the medical treatment tool further comprises a first wiring configured to supply electrical energy to the electric heater, and the first wiring is formed on a surface of the energy insulator and comprises a conductive film conducting the electrical energy.

11. The medical treatment tool according to claim 9, further comprising a first wiring configured to supply electrical energy to the electric heater, wherein the first blade, the electric heater, the first wiring, and the energy insulator are stacked in a width direction of the first jaw, the width direction being orthogonal to the opening and closing direction.

12. The medical treatment tool according to claim 1, wherein the supply surface and the output surface are perpendicular to each other.

13. The medical treatment tool according to claim 1, wherein a dimension of the supply surface in the opening and closing direction is greater than a dimension of the supply surface in a direction perpendicular to the opening and closing direction.

14. A medical treatment tool comprising: a grasping portion having a first jaw and a second jaw configured to be opened and closed, wherein the first jaw comprises: a first blade having: an output surface facing the second jaw; and a heat receiving surface; and an energy supply portion having a supply surface, the energy supply portion configured to supply treatment energy to the heat receiving surface of the first blade via the supply surface of the energy supply portion; the supply surface being elongated in an opening and closing direction of the grasping portion such that a dimension of the supply surface in the opening and closing direction is greater than a dimension of the supply surface in a direction perpendicular to the opening and closing direction; and the supply surface having an area larger than an area of the output surface.

15. The medical treatment tool according to claim 14, wherein the treatment energy is ultrasonic waves, and the energy supply portion is an ultrasonic vibrator.

16. The medical treatment tool according to claim 14, wherein the output surface extends along a width direction of the first jaw, the width direction being orthogonal to the opening and closing direction.

* * * * *